United States Patent [19]

Hart

[11] Patent Number: 5,474,141

[45] Date of Patent: Dec. 12, 1995

[54] APPARATUS FOR OBTAINING A SOIL CORE SAMPLE

[76] Inventor: Ronald D. Hart, 1910 Fairview Ave. East, Seattle, Wash. 98102-3699

[21] Appl. No.: 370,782

[22] Filed: Jan. 10, 1995

[51] Int. Cl.$^6$ .............................. E21B 49/02; G01N 1/08
[52] U.S. Cl. ........................... 175/20; 73/864.44; 175/58
[58] Field of Search .............................. 175/20, 58, 251, 175/254; 73/864.44, 864.45; 172/22; 111/92, 99

[56] References Cited

U.S. PATENT DOCUMENTS

| 828,527 | 8/1906 | Ankeny | 73/864.44 |
|---|---|---|---|
| 1,919,461 | 7/1933 | Burke et al. | 175/58 |
| 3,667,553 | 6/1972 | Gill | 175/20 X |

FOREIGN PATENT DOCUMENTS

| 2003534 | 3/1979 | United Kingdom | 175/58 |
|---|---|---|---|
| 2218441 | 11/1989 | United Kingdom | 175/20 |

*Primary Examiner*—Stephen J. Novosad
*Attorney, Agent, or Firm*—Nies, Kurz, Bergert & Tamburro

[57] ABSTRACT

Soil sampling apparatus for forming and containing a core sample of a predetermined depth of soil into which the soil sampling apparatus is driven. A pair of cooperable, core-defining core tube members are carried on a guide rod and are individually and sequentially driven into the soil to be sampled. The core tube members include angularly positioned panels for increased torsional rigidity, and the apparatus includes a cam and follower arrangement for permitting automatic circumferential orientation of one core tube member relative to the other core tube member before interengagement of the core tube members to define a complete core tube. The core tube members are each pointed at their lower ends to more easily penetrate the soil, and one core tube member includes a pivotable soil sample gate to retain the soil sample within the core tube as the core tube is withdrawn from the soil.

15 Claims, 4 Drawing Sheets

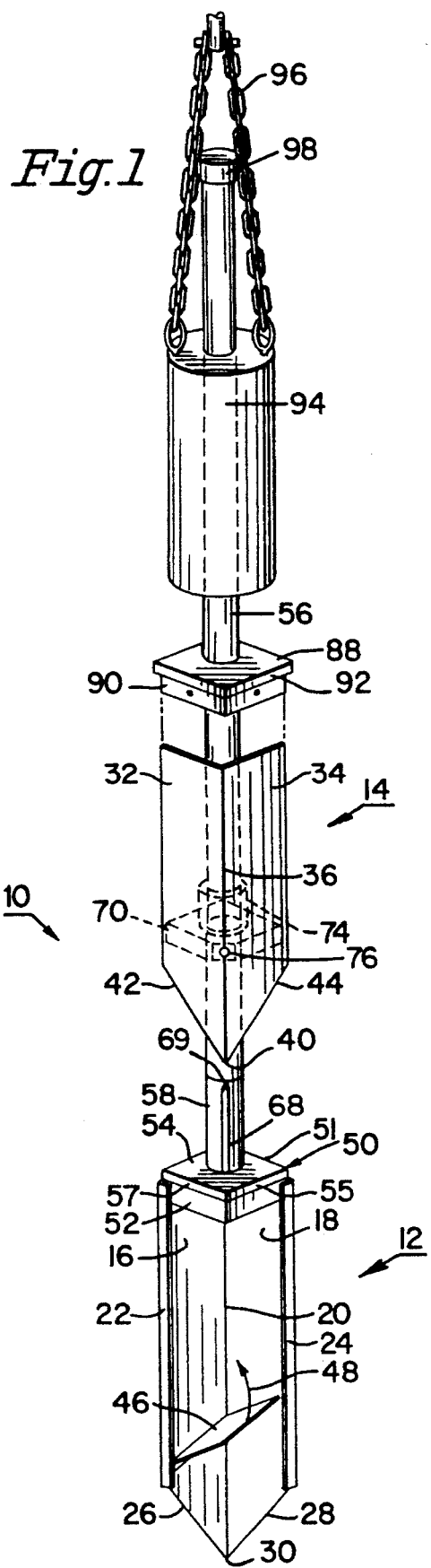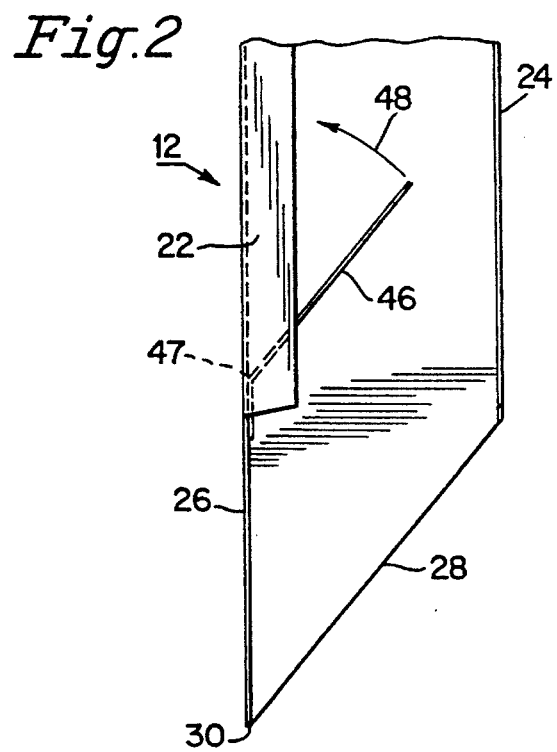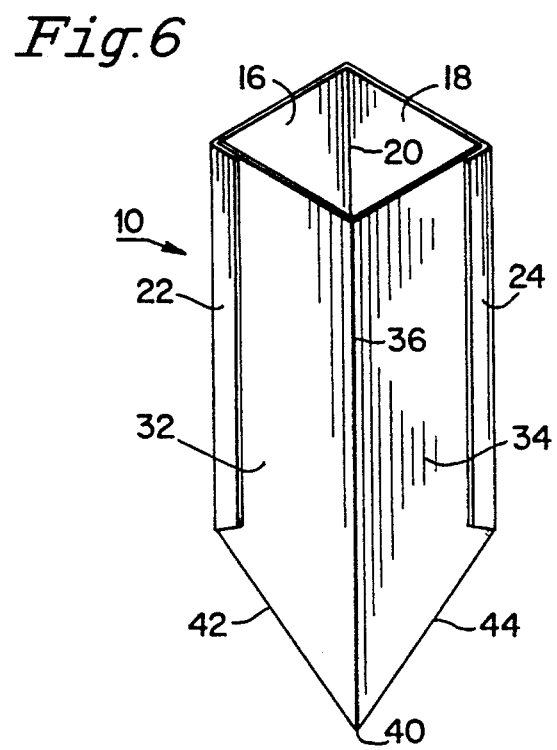

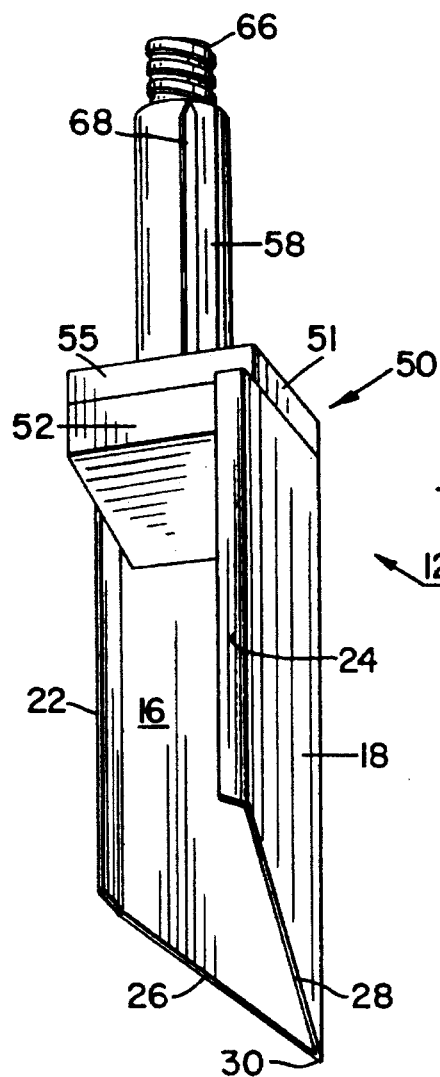
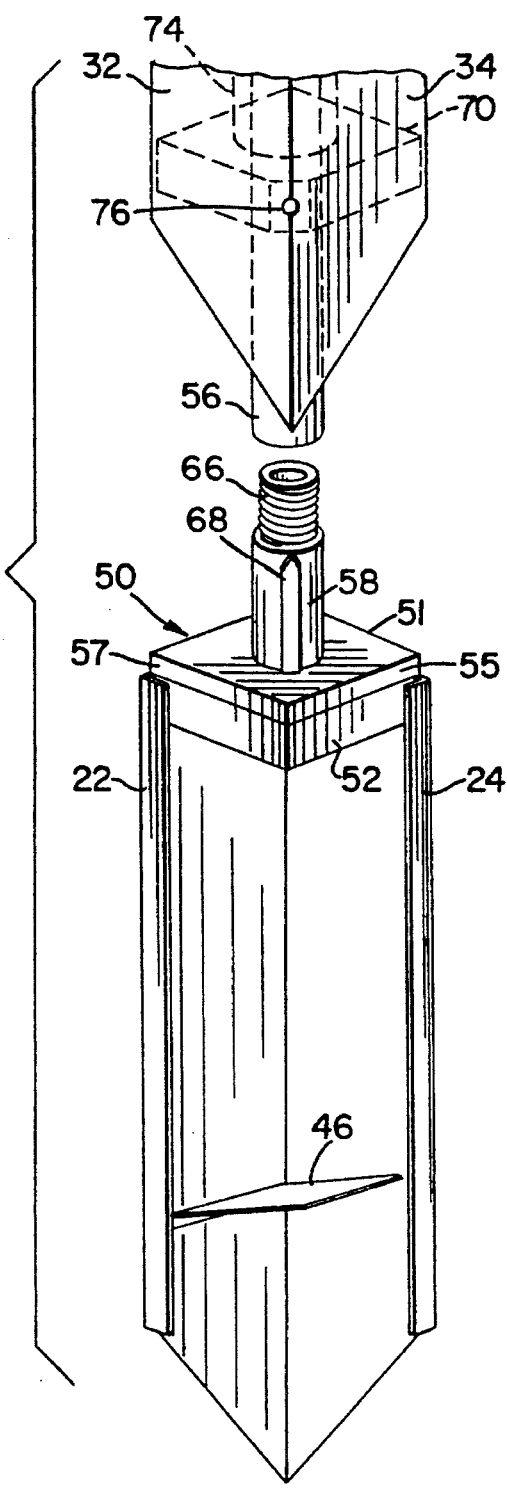

APPARATUS FOR OBTAINING A SOIL CORE SAMPLE

BACKGROUND OF THE INVENTION

1. Field of the Invention

The present invention relates to soil sampling apparatus for obtaining a core sample of a predetermined depth of soil by driving the apparatus into the soil to be sampled. More particularly, the present invention relates to a tubular soil sampling apparatus having two interengaging portions to provide an elongated core of soil, wherein the individual portions are remote from the operator and are sequentially driven into the soil to be sampled, and wherein the interengaging portions are automatically properly oriented relative to each other prior to interengagement.

2. Description of the Related Art

Soil sampling devices for providing a core of soil by driving a tubular member into the soil to be sampled are well known. For example, U.S. Pat. No. 828,527, which issued on Aug. 14, 1906, to O. P. Ankeny, discloses a soil sampling device including a pair of interengaging, core-defining halves that are individually and sequentially driven into the soil to be sampled. The Ankeny device is adapted to be manually driven into the sand by means of cross-bars or handles that are carried by each of the respective sampler portions.

Another form of soil sampling device is disclosed in U.S. Pat. No. 1,919,461, which issued Jul. 25, 1933, to R. H. Burke et al. The Burke et al patent also discloses a soil core sampling device utilizing a pair of cooperating portions that are individually driven into the earth and then retracted with the core sample contained within the interengaged sampling device portions.

Although the Ankeny and the Burke et al. devices are suitable for their intended purpose, they are very rudimentary devices and are only usable in instances where the soil to be sampled is immediately accessible to the operator taking the core sample. Thus, if it is desired to take a core sample of soil at the bottom of a body of water, the structures of the Ankeny and Burke et al devices are such that the operator would be required to be standing in the body of water, and to apply driving forces to the ends of the core tube members while they and the operator were below the surface of the water, except for very shallow bodies of water.

The present applicant developed an improved soil core sampling device that has the structure and that operates as described in his U.S. Pat. No. 5,322,133, which issued on Jun. 21, 1994. That device overcomes the deficiencies of the earlier devices and provides an improved soil core sampling device that can provide a core sample of the earth or sediment below a body of water and at a position remote from the operator. It also enables remote alignment, such as from a boat, of the two parts of a two part soil core sampler while the sampler is below the water surface and is immediately adjacent the soil to be sampled.

SUMMARY OF THE INVENTION

Briefly stated, in accordance with one aspect of the present invention, soil sampling apparatus is provided for obtaining a core sample of a predetermined depth of soil into which the soil sampling apparatus is driven. The apparatus includes a first elongated core tube member having a longitudinal axis and a first anvil surface for driving the first core tube member into the soil to be sampled.

A second elongated core tube member is provided and is longitudinally slidably engagable with the first core tube member to define therewith a tubular sample holder having an inner volume to receive soil as the tube members are respectively sequentially driven into the soil to be sampled. The second core tube member includes a second anvil surface for driving the second core tube member into the soil to be sampled.

An elongated guide rod is connected with the first core tube member and extends substantially parallel with the longitudinal axis of the first core tube member. A holder is provided for holding the second core tube member, wherein the holder is carried by the guide rod for longitudinal sliding movement therealong and for guiding the second elongated core tube member into cooperative engagement with the first core tube member.

A drive weight is provided and is removably carried by the guide rod for longitudinal movement along the guide rod, and for striking the respective anvil surfaces of the first and second core tube members for sequentially driving the first and second core tube members into the soil to be sampled.

An alignment arrangement is provided to automatically properly align and orient the first core tube member relative to the second core tube member in a circumferential direction to permit subsequent engagement therebetween to define a core tube.

BRIEF DESCRIPTION OF THE DRAWINGS

FIG. 1 is a side view, in perspective, showing the several elements of one form of soil sampling apparatus in accordance with the present invention.

FIG. 2 is a fragmentary, side elevational view of the lowermost portion of the soil sampling apparatus illustrated in FIG. 1, showing a sample gate for retaining the soil sample within the apparatus during removal of the apparatus from the soil into which it has been driven.

FIG. 3 is a perspective view of a first core tube member, looking upwardly and inwardly to show the inner structure of the first core tube member and the arrangement for connection with the guide rod that forms part of the soil apparatus shown in FIG. 1.

FIG. 4 is a perspective view of a first core tube member, looking downwardly and inwardly, and a portion of a second core tube member before connection of the guide rod with the first core tube member.

FIG. 6 is a perspective view showing in assembled form the first and second core tube members of the soil sampling apparatus shown in FIG. 1, for defining and enclosing a soil sample to be withdrawn from a mass of soil.

DESCRIPTION OF THE PREFERRED EMBODIMENTS

Figure 5:
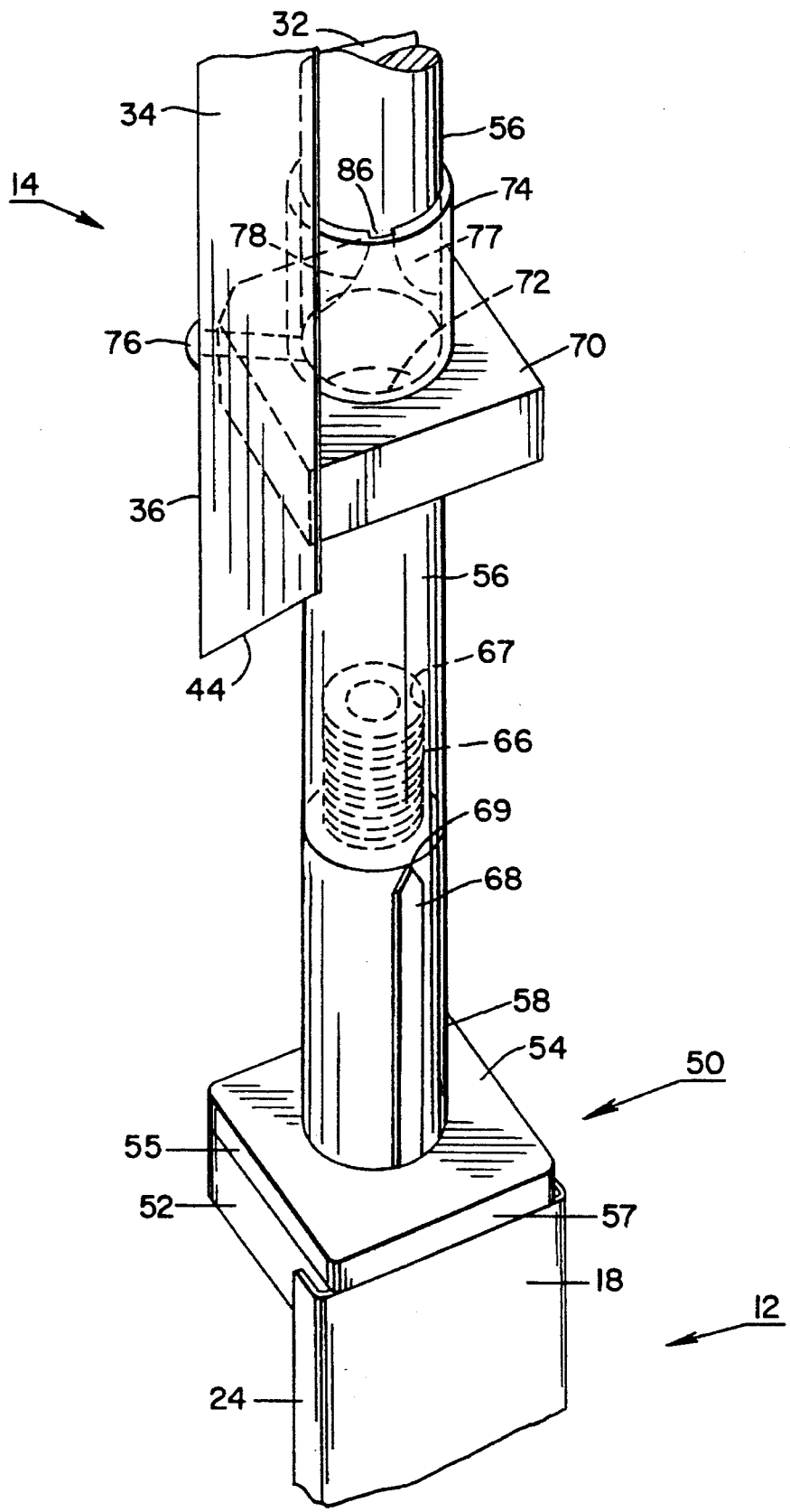
FIG. 5 is a fragmentary perspective view showing the interconnections with the guide rod of the first and second core tube members.

Referring now to the drawings, and particularly to FIG. 1 thereof, there are shown the several parts of a soil sampling apparatus in accordance with the present invention, in which the several parts of the apparatus are shown in their relative operative positions immediately before the apparatus is driven into soil to be sampled. A core sample tube 10 of rectangular cross section is defined by a first core tube member 12, and a second core tube member 14. The respective core tube members 12 and 14 are shown displaced from each other in FIG. 1, but are shown in engaged, assembled condition in FIG. 6.

First core tube member 12 includes first and second longitudinally extending rectangular panel members 16 and 18, respectively, which are preferably positioned at right angles to each other and are joined along a longitudinally extending edge or corner 20. First panel member 16 includes a flange 22 that extends perpendicularly from and along the free longitudinal edge of panel member 16 and is substantially parallel with second panel member 18. Similarly, second panel member 18 includes a flange 24 that extends perpendicularly from and along the free longitudinal edge of panel member 18 and is substantially parallel with first panel member 16. Additionally, first core tube member 12 is so configured that the lowermost edges 26, 28 of panel members 16 and 18, respectively, are inclined to define a pointed lower end 30 to facilitate driving first core tube member 12 into the soil to be sampled.

Second core tube member 14 is configured similarly to first core tube member 12 in that it includes first and second panel members 32 and 34 that are positioned at right angles to each other and that are joined along a longitudinally extending edge or corner 36. Unlike first core tube member 12, however, second core tube member 14 does not include any longitudinal flanges. Additionally, second core tube member 14 is so sized as to be longitudinally slidably received within first core tube member 12 so that the outer longitudinal edges of each of panels 32 and 34 are adjacent to and preferably in contact with the inwardly facing surfaces of flanges 22 and 24, respectively, of first core tube member 12. As was the case for first core tube member 12, second core tube member 14 is also so configured as to provide a pointed lower end 40 by inclining the lowermost edges 42 and 44 of side panels 32 and 34, respectively. With respect to each of first core tube member 12 and second core tube member 14, the two-sided angular structure provides core tube members having greater strength and greater torsional rigidity, as compared with core tube members that are merely curved in transverse cross section.

In use, first core tube member 12 is first driven into the soil to be sampled in a direction parallel with the longitudinal axis of core tube member 12, and then second core tube member 14 is positioned as shown in FIG. 1 and then is also driven in the same direction into the soil to be sampled to, in essence, cut from the body of soil a longitudinally extending sample having a rectangular or square cross section. After having been driven into the soil, first and second core tube members 12 and 14 are interengaged and are in the relative positions shown in FIG. 6, to define a rectangular container. The interengaged core tube members are then withdrawn together from the soil to be sampled, with a soil sample therebetween, whereupon the core tube members can be separated to remove the soil sample ample for analysis, if desired.

Retention of the soil sample within the assembled first and second core tube members 12 and 14, which when assembled are disposed as shown in FIG. 6, is accomplished by providing a sample gate 46, which is shown in FIGS. 1 and 2. In that regard, sample gate 46 is preferably pivotally connected with the innermost face of panel 16, by a hinge 47, or the like, and at a position adjacent the lowermost end of first core member 12, but spaced slightly above the lowermost end of flange member 22. Thus, as first core tube member 12 is driven into the soil to be sampled, sample gate 46 is initially pivoted in the direction shown by arrows 48 in each of FIGS. 1 and 2. Upon attempted withdrawal together of the first and second core tube members 12 and 14 after each has been driven into the soil to be sampled, sample gate 46 is urged by the moving soil within the tube member 10 in the opposite direction from that represented by arrow 48, so that soil contained within the assembled core tube member is restrained from sliding downwardly and outwardly along the respective core tube members 12 and 14 toward pointed lower ends 30 and 40.

Referring once again to FIG. 1, first core tube member 12 carries at its uppermost end a first anvil member 50, which as shown extends transversely relative to the longitudinal axis of first core tube member 12. Anvil member 50 includes a central body portion 52 adapted to be received within the interior of first core tube member 12 at the uppermost end thereof. Anvil member 50 includes an end cap 51 positioned above and in contact with body portion 52, and that extends outwardly to overlie the uppermost edges of each of panel members 16 and 18 of first core tube member 12, so that the uppermost surface 54 of anvil member 50 is positioned to receive impact forces that are applied to cause first core tube member 12 to be driven into and to penetrate the soil to be sampled. End cap 51 serves to simultaneously transfer to the uppermost edges of each of panels 16 and 18 the forces of the driving blows applied to uppermost surface 54 of anvil member 50. As is apparent from FIGS. 3 and 4, sidewalls 55, 57 of end cap 51 that do not abut either of side panels 16 or 18 are spaced inwardly of flanges 22 and 24, in order to permit second core tube member 14 to slide over those side surfaces during use of the device, as will hereinafter be explained. Additionally, as is evident in FIG. 5, a lateral gap between flange 24 and sidewall 55 defines a slot to longitudinally slidably receive the free longitudinal edge of second panel member 34 of second core tube member 14. A similar slot is defined by the lateral gap between flange 22 and sidewall 57.

As shown in FIGS. 3 and 4, a tubular support sleeve 58 extends upwardly from and is non-rotatably and securely connected with first anvil member 50, such as by welding. Support sleeve 58 preferably is coaxial with core sample tube 10 and includes an externally threaded, reduced diameter upper end 66 that is received in a correspondingly internally threaded bore 67 in the lower end of guide rod 56 to permit connection of sleeve 58 with guide rod 56. Support sleeve 58 also includes a longitudinally extending external ridge defining a key member 68 that is preferably of rectangular cross section. Key member 68 terminates at its uppermost end, in the orientation as shown in the drawings, in a pointed, substantially triangular tip 69 that defines a pair of oppositely inclined cam follower surfaces (see FIGS. 4 and 5) for a purpose to be hereinafter described. Thus, when the parts are assembled as illustrated in FIG. 5, guide rod 56 and attached sleeve 58 define a continuous and uninterrupted cylindrical guide surface that is attached to and extends upwardly from first core tube member 12.

Referring to FIG. 1, second core tube member 14 is supported on guide rod 56 by a holder in the form of an orientation collar 70 that is slidably received on guide rod 56 to permit second core tube member 14 to be axially movable along guide rod 56. As shown in FIG. 5, collar 70 extends transversely relative to the longitudinal axis of second core tube member 14, preferably at a point adjacent to but spaced slightly upwardly from lowermost edges 42 and 44. Collar 70 is removably connected with second core tube member 14 by means of a frangible connector 76 in the form of a pin, rivet, or screw. Frangible connector 76 extends through an aperture in second core tube member 14, such as at edge 36, and is securely received in collar 70, such as in a threaded bore (not shown), or the like, as will be appreciated by those skilled in the art.

Frangible connector 76 can advantageously be made from a plastic material, such as, for example, nylon, or the like, to firmly connect second core tube member 14 with collar 70. Preferably, the material from which connector 76 is made can be severed when a force of sufficient magnitude is applied at the uppermost end of second core tube member 14, while collar 70 is held stationary, to cause connector 76 to be sheared. After connector 76 has been sheared, the connection between second core tube member 14 and collar 70 is released, to permit movement of second core tube member 14 in an axial direction relative to 56, as will be hereinafter described.

Collar 70 includes a central circular opening 72 that has a longitudinal axis that is coaxial with the axis of guide rod 56, and that has a size to permit collar 70 to be freely slidable along the outer surface of guide rod 56. Extending upwardly from collar 70 and coaxial with opening 72 and with guide rod 56 is a tubular guide sleeve 74 that surrounds and is also slidably carried on guide rod 56, along with collar 70, to permit collar 70 and attached second core tube member 14 to be slidably moved along guide rod 56 as a unit, toward and away from first core tube member 12.

Figure 5A:
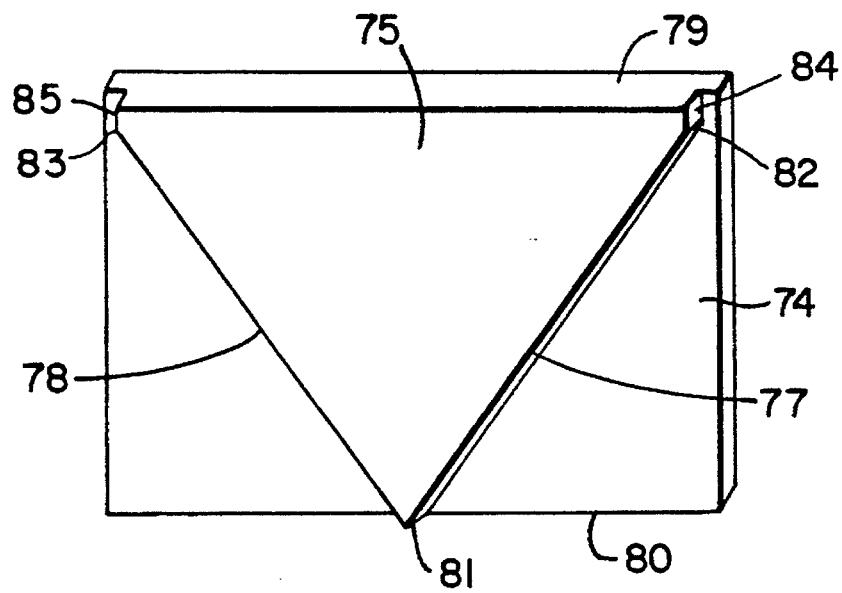
FIG. 5A is a perspective view of an unrolled tubular sleeve forming part of an orienting device in accordance with the present invention.

As best seen in FIGS. 5, 5A, 5B, and 5C, guide sleeve 74 has an inner cylindrical surface 75 that includes a pair of transverse cam surfaces 77 and 78. FIG. 5A is a development of guide sleeve 74 in which the tubular sleeve has, in effect, been severed along a peripheral longitudinal line and flattened to show the structure of the interior surface of sleeve 74.

Figure 5B:
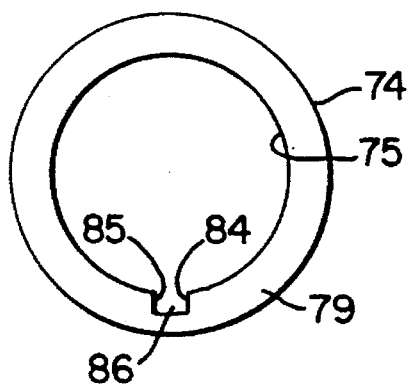
FIG. 5B is a top end view of the tubular sleeve shown in unrolled form in FIG. 5A.
Figure 5C:
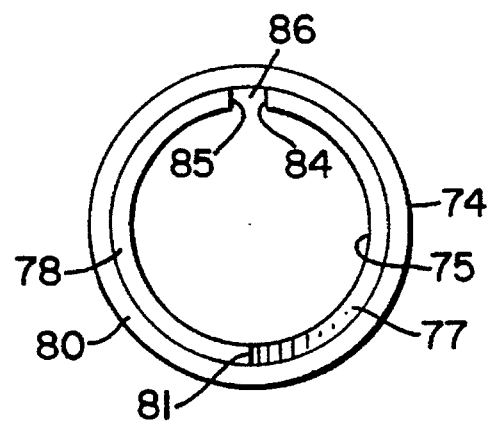
FIG. 5C is a bottom end view of the tubular sleeve shown in unrolled form in FIG. 5A.

Each of cam surfaces 77 and 78, which are shown to be linear in FIG. 5A, but which can, if desired, be curved, is inclined relative to the axis of sleeve 74, and extends in a substantially helical direction within guide sleeve 74, from the uppermost end 79 of guide sleeve 74 to the lowermost end 80 thereof. Each cam surface also extends in a different circumferential direction along inner surface 75, to meet at a lower junction point 81. The uppermost ends 82 and 83 of each of cam surfaces 77, 78, respectively, terminate at respective axially extending guide surfaces 84 and 85 to define therebetween a gap 86, as best seen in FIGS. 5B and 5C. The circumferential width of gap 86 is of such a size as to freely slidably receive key member 68 carried by support sleeve 58.

Referring once again to FIG. 1, although there shown as separated from second core tube member 14 for purposes of clarity of illustration, a second anvil member 88 is provided and is also slidably received on guide rod 56. Second anvil member 88 is positioned in overlying, contacting relationship with second core tube member 14 and is constructed in a manner similar to first anvil member 50, in that it includes a body portion 90 and an end cap 92 that extends laterally to overlie the uppermost edges of panels 32 and 34 of second core tube member 14.

Slidably carried on guide rod 56 above second anvil member 88 is a drive weight 94, to the upper end of which is connected a chain or rope to permit drive weight 94 to be remotely lifted and moved upwardly along guide rod 56. Upward movement of drive weight 94 is restricted by a removably attached end cap 98 that has a radially extending flange of sufficient extent to bear against the uppermost end of drive weight 94, to permit the entire soil sampling assembly as shown in FIG. 1 to be lifted by pulling upwardly on chain 96 until the uppermost end of drive weight 94 contacts end cap 98.

In operation, the several parts of the apparatus are arranged relative to each other as shown in FIG. 1, except that second core tube member 14, along with associated collar 70 and second anvil member 88, are initially not present on guide rod 56. The apparatus in its initial condition therefore includes only first core tube member 12 and attached first anvil member 50, guide rod 56, and drive weight 94.

The apparatus is first positioned above the soil surface into which the core tube members are intended to be driven for extracting a soil sample. Pointed lower end 30 of first core tube member 12 is brought into contact with the surface of the soil, and downward movement of first core tube member 12 into the soil to be sampled is effected by alternately lifting and dropping drive weight 94 so that it slides along guide rod 56 to act as a hammer and to provide impact forces against the uppermost surface 54 of first anvil member 50, to drive first core tube member 12 to an appropriate depth into the soil to be sampled.

When the desired depth of penetration of first core member 12 into the soil has been achieved, end cap 98 is removed from guide rod 56 and drive weight 94 is lifted and is withdrawn from guide rod 56. Collar 70, together with attached second core tube member 14, which includes anvil member 88, is then slipped onto guide rod 56 so that second anvil member 88, second core tube member 14, and collar 70 can slide downwardly along guide rod 56 as a unit.

Correct orientation of second core tube member 14 relative to first core tube member 12, so that the core tube members when interengaged define a circumferentially closed tube, occurs automatically. The correct orientation results from the cooperation between triangular tip 69 of key member 68 associated with first guide tube member 12, and cam surfaces 77 and 78 of guide sleeve 74, associated with second guide tube member 14.

If second core tube member 14 is initially correctly aligned relative to first core tube member 12, downward movement of guide sleeve 74 will result in the passage of key member 68 directly into and through gap 86 on the interior surface of guide sleeve 74, to enable subsequent engagement of the core tube members to provide the core tube member shown in FIG. 6. More likely, however, second core tube member 14 is initially circumferentially misaligned relative to first core tube member 12. In that event, downward movement of guide sleeve 74 will normally take place without significant rotation of second core tube member 14 relative to guide rod 56, until collar 70 passes tip 69 of key member 68. Thereafter, tip 69 comes into contact with one of cam surfaces 77 or 78, and because of the angular orientation of the cam surfaces relative to the longitudinal axis of guide rod 56, continued downward movement of guide sleeve 74 is accompanied by simultaneous rotation of guide sleeve 74 relative to the axis of guide rod 56. As tip 69 moves along either of cam surfaces 77 or 78, depending upon the initial orientation of second core tube member 14 relative to first core tube member 12, the inclined cam surface moves against tip 69 to cause rotation of second core tube member 14 in the proper direction until tip 69 passes one of lower junction points 80 or 81 and enters gap 86. When tip 69 enters gap 86, the rotation of guide sleeve 74 relative to guide rod 56 is stopped, and continued movement of second core tube member 14 is confined to linear downward movement as gap 86 on the interior of guide sleeve 74 moves linearly downwardly along key member 68.

When key member 68 is within gap 84, collar 70 and attached second core tube member 14 will descend linearly downwardly along support sleeve 58 until the lowermost surface of collar 70 comes into contact with the uppermost surface 54 of first anvil member 50. At that point second core tube member 14 will be in proper endwise orientation with first core tube member 12. When the core tube members are in that position, the free longitudinal edges of panels 32 and 34 of second core tube member 14 are aligned with the slot defined between flange member 22 and side wall 57 of end cap 51, and the slot defined between flange member 24 and side wall 55 of end cap 51, respectively. Thus, by virtue of the cam and follower arrangement embodied in the structure of key member 68 and of cam surfaces 77 and 78 and gap 86 of guide sleeve 74, proper relative circumferential orientation of the core tube members occurs automatically and without operator intervention.

Drive weight 94 is then slipped onto guide rod 56, after initially removing end cap 98, whereupon end cap 98 is reapplied to the uppermost end of guide rod 56. Weight 94 is again alternately raised and allowed to drop, now to fall against the uppermost surface of second anvil member 88, to shear frangible connector 76 and thereby allow separation of second core tube member 14 from collar 70. Continued blows from drive weight 94 against second anvil member 88 cause second core tube member 14 to be driven into the soil to be sampled, and into cooperative engagement with first core tube member 12 to ultimately assume the relative orientation of the core tube members as shown in FIG. 6.

After second core tube member 14 has been driven the desired distance into the soil, drive weight 94 is lifted until its uppermost surface engages end cap 98. Repeatedly pulling drive weight 94 upwardly against end cap 98 in a series of hammer-like blows serves to slowly remove the entire assembly of guide rod 56 and associated core sample tube 10 from the soil to be sampled, with the soil core sample contained within the tubular structure 10 defined by interengaged first and second core tube members 12 and 14. As was noted earlier, the soil sample is retained within the core tube by means of sample gate 46, which serves to prevent the soil sample from sliding downwardly as the core tube is withdrawn.

It will be apparent that the present invention provides distinct advantages over the prior art arrangements, in that it permits simplified extraction of a soil core sample remotely, for example from beneath the surface of a body of water. In the latter case, guide rod 56 must be of sufficient length to extend from a vessel on the surface of the body of water to the surface of the soil below the body of water. Additionally, the present invention can provide a soil sample of a desired depth below the soil surface by providing first and second core tube member of sufficient axial length.

Although the right-angled core tube members illustrated herein define a square tube, they can also be so configured as to form a rectangular or diamond shaped soil core cross section, if desired. In any event, use of two angled core tube members provides increased torsional rigidity to each of the core tube members, which facilitates driving the members into difficult-to-penetrate soils. Moreover, because each of the core tube members includes a pointed lower end, penetration of the core tube members into the soil to be sampled is greatly facilitated.

Although particular embodiments of the invention have been illustrated and described, it will be apparent to those skilled in the art that various changes and modifications can be made without departing from the spirit of the present invention. It is therefore intended to encompass within the appended claims all such changes and modifications that fall within the scope of the present invention.

What is claimed is:

1. Soil sampling apparatus for obtaining a core sample of a predetermined depth of soil into which the soil sampling apparatus is driven, said apparatus comprising:

a) a first elongated core tube member having a longitudinal axis and a first anvil surface for driving the first core tube member into soil to be sampled;

b) a second elongated core tube member longitudinally slidably engagable with the first core tube member to define therewith a tubular sample holder having an inner volume to receive soil as the tube members are respectively sequentially driven into the soil to be sampled, the second core tube member including a second anvil surface for driving the second core tube member into the soil to be sampled;

c) an elongated guide rod connected with the first core tube member and extending substantially parallel with the longitudinal axis of the first core tube member;

d) a holder connected with the second core tube member for holding the second core tube member, the holder engaging with and carried by the guide rod for longitudinal sliding movement along the guide rod and for positioning the second elongated core tube member so it can be axially guided into cooperative engagement with the first core tube member;

e) a drive weight removably carried by the guide rod for longitudinal movement along the guide rod and for sequentially striking the respective anvil surfaces of the first and second core tube members for sequentially driving the first and second core tube members into the soil to be sampled; and f) alignment means for circumferentially aligning the first and second core tube members relative to each other as the core tube members are brought together to permit longitudinal engagement therebetween to define a core tube.

2. Soil sampling apparatus in accordance with claim 1 wherein the alignment means rotates the second core tube member relative to the longitudinal axis of the first core tube member.

3. Soil sampling apparatus in accordance with claim 1 wherein the alignment means operates to rotate the second core tube member into an aligned position relative to the first core tube member as the second core tube member moves along the guide rod toward the first core tube member.

4. Soil sampling apparatus in accordance with claim 1 wherein the alignment means includes a cam and a cam follower engagable with the cam for relatively rotating the second core tube member and the first core tube member into a circumferentially aligned position.

5. Soil sampling apparatus in accordance with claim 4 wherein the cam is carried by the second core tube member and the cam follower is carried by the guide rod.

6. Soil sampling apparatus in accordance with claim 5 wherein the cam includes a helical cam surface carried by a sleeve connected with the second core tube member and slidably carried on the guide rod.

7. Soil sampling apparatus in accordance with claim 5 wherein the cam is defined by a pair of oppositely oriented helical surfaces that converge in a direction away from the first core tube member to terminate at a gap having a size to slidably receive the cam follower.

8. Soil sampling apparatus in accordance with claim 5 wherein the cam is formed on an inner peripheral surface of a tubular sleeve carried by the second core tube member for sliding engagement with the guide rod.

9. Soil sampling apparatus in accordance with claim 8 wherein the cam follower is a longitudinally extending peripheral key member carried by the guide rod and having a size to permit the key member to pass through the gap.

10. Soil sampling apparatus in accordance with claim 9 wherein the key member includes a pair of oppositely inclined cam follower surfaces defining a substantially triangular tip for engagement with a surface of the cam.

11. Soil sampling apparatus in accordance with claim 9 wherein the key member has an axial length sufficient to engage the gap during movement of the second core tube member toward the first core tube member before and after initial engagement of the core tube members to define a core tube.

12. Soil sampling apparatus in accordance with claim 1 including a sample gate pivotably carried on an interior surface of one of the first core tube member and the second core tube member for pivotal movement into an inner volume defined by the core tube members when they are engaged to define the tubular sample holder after the tube members have been driven into the soil to be sampled, to block egress of the soil from the sample holder as the sample holder is being withdrawn from the soil to be sampled.

13. Soil sampling apparatus in accordance with claim 1 wherein the holder is connected with the second core tube member by a frangible connection.

14. Soil sampling apparatus in accordance with claim 6 wherein the frangible connection is a shear pin that extends between and interconnects the holder with the second core tube member.

15. Soil sampling apparatus in accordance with claim 7 wherein the shear pin is a nylon pin.

* * * * *